United States Patent
Ishige et al.

(10) Patent No.: US 11,852,571 B2
(45) Date of Patent: Dec. 26, 2023

(54) SAMPLE SEPARATION DEVICE AND SAMPLE SEPARATION METHOD

(71) Applicant: HITACHI, LTD., Tokyo (JP)

(72) Inventors: Yu Ishige, Tokyo (JP); Sakuichiro Adachi, Tokyo (JP); Takahiro Ando, Tokyo (JP)

(73) Assignee: HITACHI, LTD., Tokyo (JP)

(*) Notice: Subject to any disclaimer, the term of this patent is extended or adjusted under 35 U.S.C. 154(b) by 575 days.

(21) Appl. No.: 16/966,782

(22) PCT Filed: Nov. 2, 2018

(86) PCT No.: PCT/JP2018/040833
§ 371 (c)(1),
(2) Date: Jul. 31, 2020

(87) PCT Pub. No.: WO2019/187299
PCT Pub. Date: Oct. 3, 2019

(65) Prior Publication Data
US 2020/0355585 A1   Nov. 12, 2020

(30) Foreign Application Priority Data

Mar. 30, 2018   (JP) .................................. 2018-070353

(51) Int. Cl.
*G01N 1/40*        (2006.01)
*B01L 3/00*        (2006.01)
(Continued)

(52) U.S. Cl.
CPC ................ *G01N 1/40* (2013.01); *B01L 3/502* (2013.01); *B04B 5/0421* (2013.01); *B04B 11/04* (2013.01);
(Continued)

(58) Field of Classification Search
CPC .......... G01N 1/40; G01N 1/10; G01N 1/4077; G01N 2001/4083; G01N 2035/00495;
(Continued)

(56) References Cited

U.S. PATENT DOCUMENTS

| | | | |
|---|---|---|---|
| 4,792,432 A | 12/1988 | Ikonen | |
| 2006/0228793 A1* | 10/2006 | Cho | .................. B01L 3/502715 435/288.5 |
| 2009/0162940 A1* | 6/2009 | Wardlaw | .......... A61B 5/150213 436/180 |

FOREIGN PATENT DOCUMENTS

| | | | |
|---|---|---|---|
| GB | 2186081 | * | 8/1987 |
| JP | 62-185167 A | | 8/1987 |

(Continued)

OTHER PUBLICATIONS

International Search Report and Written Opinion for related International Application No. PCT/JP2018/040833, dated Jan. 29, 2019; English translation of ISR provided (7 pages).

*Primary Examiner* — Benjamin R Whatley
*Assistant Examiner* — Jacqueline Brazin
(74) *Attorney, Agent, or Firm* — Procopio, Cory, Hargreaves & Savitch LLP

(57) ABSTRACT

A sample separation device to introduce a sample to be separated to an inside of the sample separation device, centrifuge the sample, and collect a desired liquid after separation, includes: a sample introducing portion introducing the sample into the sample separation device; a liquid surface defining portion connected to the sample introducing portion; a first separating portion connected to the liquid surface defining portion; a second separating portion connected to the first separating portion; a third separating portion connected to the second separating portion; and a liquid extracting portion including the third separating portion and connected to the third separating portion, in which (Continued)

a tubular flow path is formed by at least the first separating portion and the second separating portion, in which an opening of the sample introducing portion and an opening of the liquid extracting portion are oriented in the same direction.

8 Claims, 14 Drawing Sheets

(51) Int. Cl.
B04B 5/04 (2006.01)
B04B 11/04 (2006.01)
G01N 1/10 (2006.01)

(52) U.S. Cl.
CPC ........ *G01N 1/10* (2013.01); *B01L 2300/0877* (2013.01); *B01L 2400/0406* (2013.01)

(58) Field of Classification Search
CPC ........... G01N 2035/1053; G01N 33/48; G01N 33/491; G01N 35/00; G01N 37/00; B01L 3/502; B01L 2300/0877; B01L 2400/0406; B01L 2200/027; B01L 2300/0838; B01L 2400/0409; B01L 2400/0688; B01L 3/502753; B04B 5/0421; B04B 11/04
USPC .......................................................... 494/37
See application file for complete search history.

(56) References Cited

FOREIGN PATENT DOCUMENTS

JP 2008-180543 A 8/2008
WO 2018/066294 A1 4/2018

* cited by examiner

FIG. 6
(a)
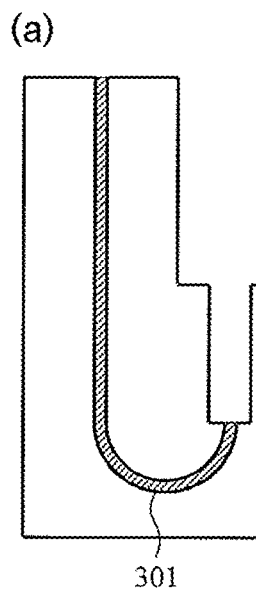
301
(b)
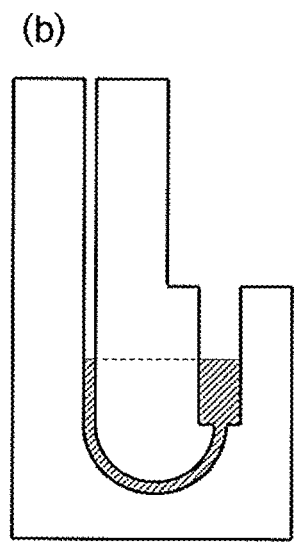
(c)
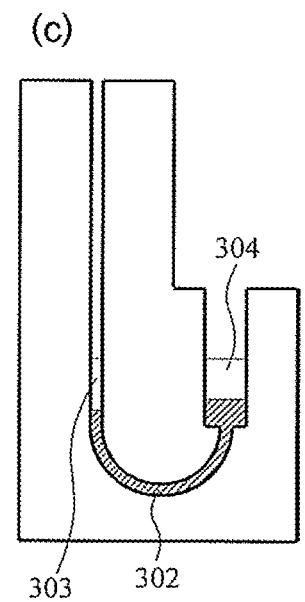
304
303  302
(d)
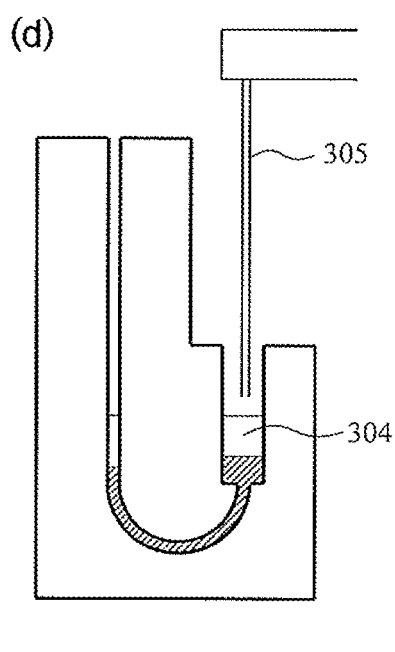
305
304
(e)
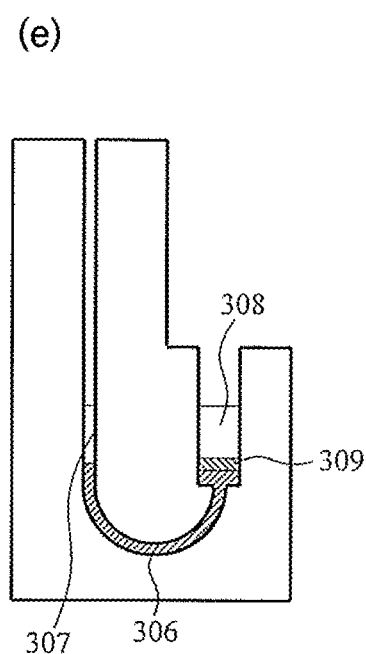
308
309
307  306

FIG. 10
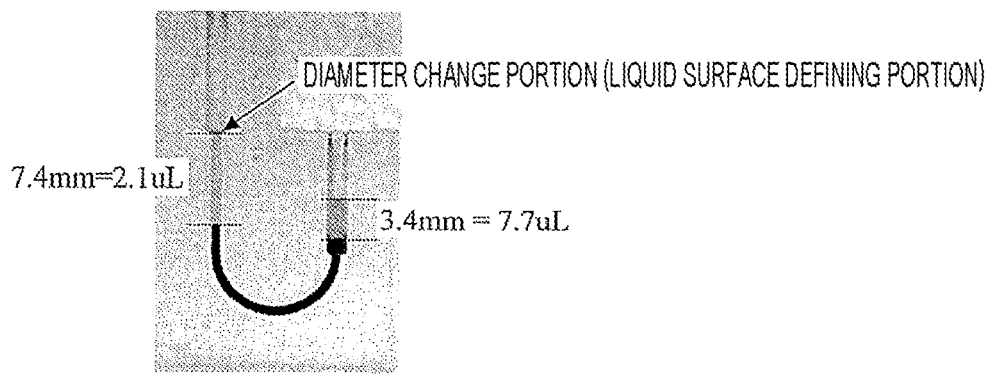
FIG. 11
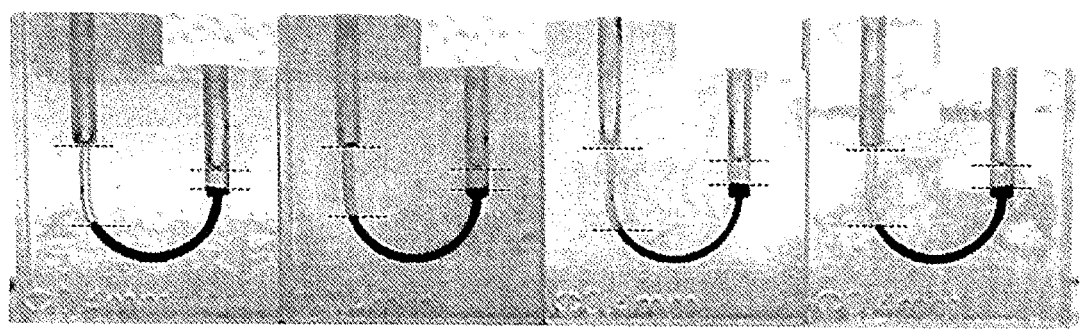
FIG. 12
(a) 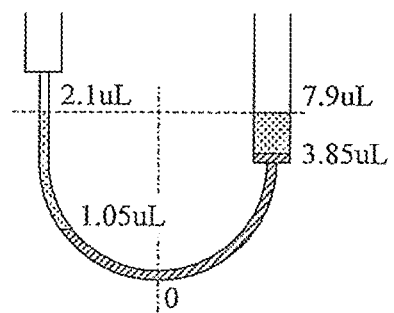   (b) 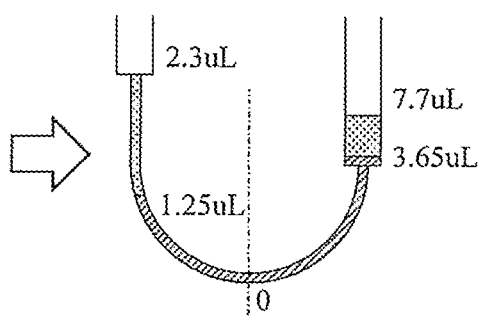

SAMPLE SEPARATION DEVICE AND SAMPLE SEPARATION METHOD

CROSS-REFERENCE TO RELATED APPLICATIONS

This application is a U.S. National Stage entry of PCT Application No: PCT/JP2018/040833 filed Nov. 2, 2018, which claims priority to Japanese Patent Application No. 2018-070353, filed Mar. 30, 2018, the contents of which are incorporated herein by reference.

TECHNICAL FIELD

The present disclosure relates to a sample separation device and a sample separation method.

BACKGROUND ART

A blood test is a quantitative and qualitative test and analysis of blood components, and is used for a diagnosis in a hospital and a regular health check. In a biochemical test or an immunological test, which is part of a blood test, analysis is performed using a liquid component called plasma or serum obtained by removing blood cell components from blood as a sample. Therefore, in these tests, there is a blood cell separation procedure for separating blood cells from plasma or serum.

In general, in blood cell separation performed in a laboratory, a method of centrifuging a blood collection tube containing several mL of blood is mainly used. Since the specific gravity of blood cells is higher than the specific gravity of plasma/serum, blood cells are separated at the bottom and plasma/serum is separated at the top. In order to improve the state of separation, a separating agent having a specific gravity which is intermediate between blood cells and plasma/serum may be used.

Further, in a test called Point-Of-Care Testing (POCT) performed in front of or near the patient's eyes, a blood test using a cartridge may be performed. At that time, centrifugation may be performed in the cartridge to separate blood cells. For example, in PTL 1, centrifugation is performed using a U-shaped flow path, and the obtained plasma is used for analysis.

CITATION LIST

Patent Literature

PTL 1: JP 2008-180543 A

SUMMARY OF INVENTION

Technical Problem

However, in the blood cell separation by centrifugation using the U-shaped flow path of PTL 1, approximately equal amounts of plasma are separated on the right and left sides of the U-shaped flow path, and only one of them is used for analysis. Therefore, as a result, only half of the purified plasma can be used for analysis, and it is desired that more plasma can be collected as an analysis target.

The present disclosure has been made in view of such a situation, and provides a technique that enables more target liquid components to be collected after centrifugation.

Solution to Problem

In order to solve the above-described problem, the present disclosure employs, for example, the configurations described in the claims. Although the present specification includes a plurality of means for solving the above-described problem, as an example, according to the present disclosure, there is provided a sample separation device used to introduce a sample to be separated to an inside of the sample separation device, centrifuge the sample, and collect a desired liquid after separation, the sample separation device including:

a sample introducing portion configured to introduce the sample to be separated into the sample separation device;

a liquid surface defining portion connected to the sample introducing portion;

a first separating portion connected to the liquid surface defining portion;

a second separating portion connected to the first separating portion;

a third separating portion connected to the second separating portion; and a liquid extracting portion including the third separating portion and connected to the third separating portion, in which a tubular flow path is formed by at least the first separating portion and the second separating portion, in which an opening of the sample introducing portion and an opening of the liquid extracting portion are oriented in the same direction, in which the first separating portion is configured so that gravity and a capillary force generated in a direction opposite to the gravity act on the sample after separation, in which a horizontal cross-sectional area of the liquid surface defining portion is larger than a horizontal cross-sectional area of the first separating portion, and an action of the capillary force on the sample after the separation is reduced when the sample after the separation reaches a lowermost portion of the liquid surface defining portion due to the capillary force.

Further features related to the present disclosure will be apparent from the description of the present specification and the accompanying drawings. Further, aspects of the present disclosure are achieved and realized by the elements and combinations of various elements, and the following detailed description and aspects of the claims.

It is to be understood that the description of the present specification is merely exemplary and is not intended to limit the claims or application examples of the present disclosure in any way.

Advantageous Effects of Invention

According to the present disclosure, it is possible to easily collect a target liquid component after centrifugation while suppressing mixing of blood cells.

BRIEF DESCRIPTION OF DRAWINGS

FIG. 1A is a diagram illustrating an appearance of the centrifuge 10. FIG. 1B is a diagram illustrating an appearance of a rotor 13 of the centrifuge 10.

FIG. 2A is a diagram illustrating the appearance of the rotor 13 of the another embodiment.

FIGS. 3A to 3D illustrate a process before an introduced blood (sample) is separated into each blood cell component.

FIG. 5A is a diagram illustrating an appearance configuration example of the blood cell separation device 201. FIG. 5B is a diagram illustrating a cross section of the blood cell separation device 201.

FIGS. 6(a) to 6(e) are diagrams illustrating a procedure of blood cell separation using the blood cell separation device 201.

FIG. 10 is a diagram illustrating the result of producing a plasma separation device in which the thickness of a small-diameter-side flow path was discontinuously increased to 1.7 mm for 20 μL of blood, and performing plasma separation under the same conditions.

FIG. 11 is a diagram illustrating the result of performing plasma separation using plasma separation devices having a diameter change portion designed for a blood amount of 10 μL.

FIGS. 12(a) to 12(b) are diagrams for describing a phenomenon in which the height of the interface becomes inconsistent between a small-diameter side and a large-diameter side in the course of causing sedimentation of blood cells due to a centrifugal force independently on left and right sides of an asymmetric U-shaped flow path.

FIG. 13A is a device for 10 μL of blood and FIG. 13B is a device for 20 μL of blood.

DESCRIPTION OF EMBODIMENTS

The present disclosure relates to a sample separation device including a flow path tube and including a liquid surface defining portion.

Hereinafter, embodiments of the present disclosure will be described with reference to the accompanying drawings. In the accompanying drawings, functionally the same elements may be represented by the same numbers. Note that the attached drawings show specific embodiments and implementation examples in accordance with the principles of the present disclosure, but these are for understanding of the present disclosure, and are not used to interpret the present disclosure in a limited manner.

Although the present embodiment has been described in sufficient detail for those skilled in the art to implement the present disclosure, other implementations and forms are possible. It is necessary to construe that the configuration/structure can be changed and various elements can be replaced without departing from the scope and spirit of the technical idea of the present disclosure. Therefore, the following description should not be construed as being limited thereto.

In the embodiments and examples described below, a blood cell separation device for separating blood cells, and plasma and serum in blood may be described as an example, but separating blood is one aspect. Thus, the device of the present disclosure is applicable to liquids other than blood. Therefore, it should be noted that the device may be referred to as a sample separation device.

<Configuration of Centrifuge>
(i) Overall Configuration

Figure 1:
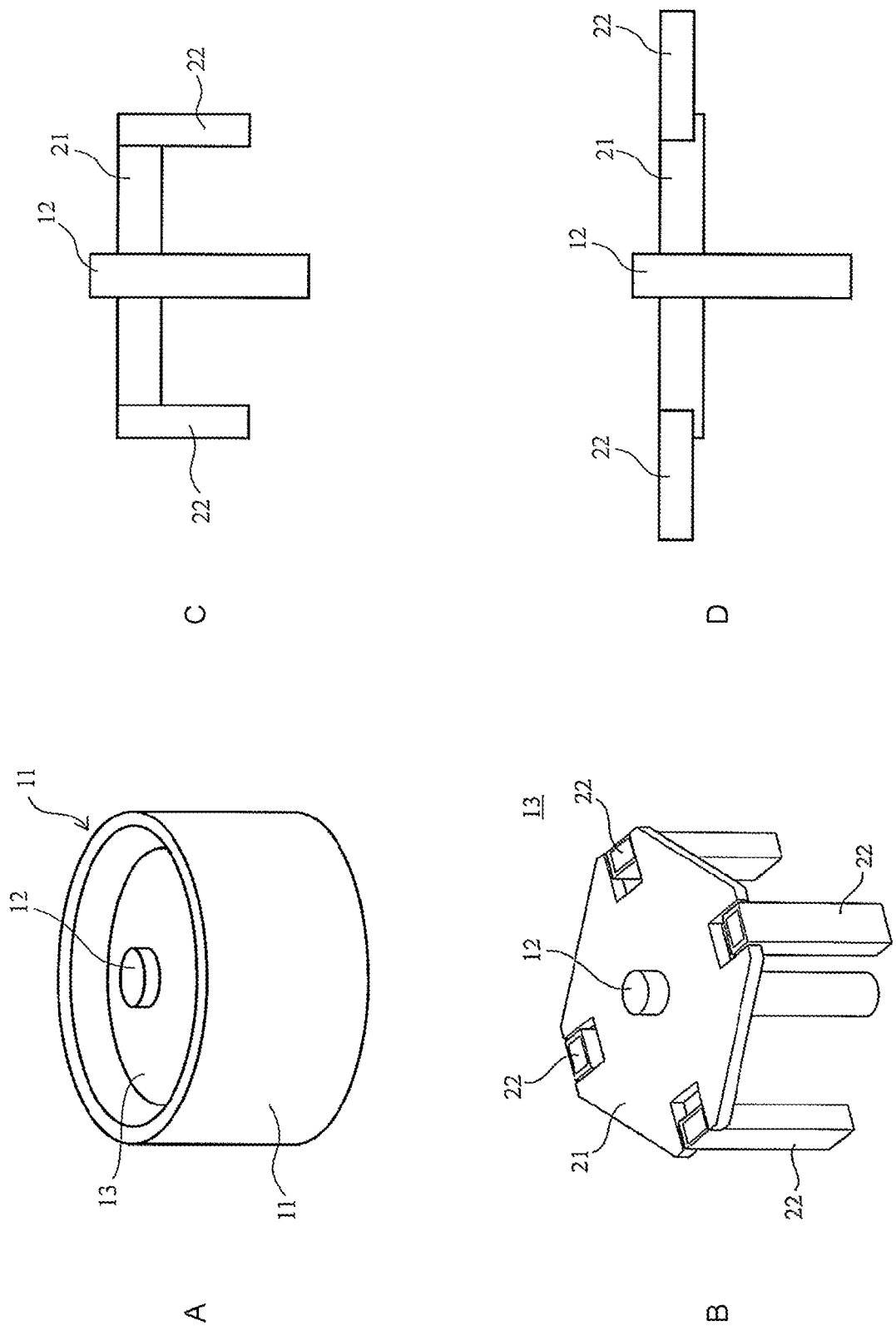
FIGS. 1A to 1D are diagrams illustrating a schematic configuration example of a centrifuge 10 used in an embodiment of the present disclosure.

FIG. 1 is a diagram illustrating a schematic configuration example of a centrifuge 10 used in an embodiment of the present disclosure. FIG. 1A is a diagram illustrating an appearance of the centrifuge 10. The centrifuge 10 includes a casing 11, and a rotor 13 which is housed in the casing 11 and rotates around a rotation shaft 12 (see FIG. 1A).

FIG. 1B is a diagram illustrating an appearance of the rotor 13 of the centrifuge 10. FIG. 1C is a diagram illustrating a state before a centrifugal force is applied to a sample separation device 100. FIG. 1D is a diagram illustrating a state when a centrifugal force is applied to the sample separation device 100.

The rotor 13 in FIG. 1 is a swing-type rotor, and includes a rotation shaft 12, a rotating disk 21 connected to the rotation shaft 12, and a plurality of movable buckets 22 provided to the rotating disk 21 (see FIG. 1B). Each of the movable buckets 22 holds the sample separation device 100, and is configured to be rotatable about a support shaft (not shown). The buckets 22 are substantially perpendicular to the rotating disk 21 before the rotor 13 rotates (see FIG. 1B), and when the rotor 13 rotates, each bucket tip 221 gradually becomes horizontal due to a centrifugal force (see FIG. 1C). The height to which the bucket tip 221 can be lifted depends on the strength of the centrifugal force.

(ii) Another Configuration Example of the Rotor 13

Figure 2:
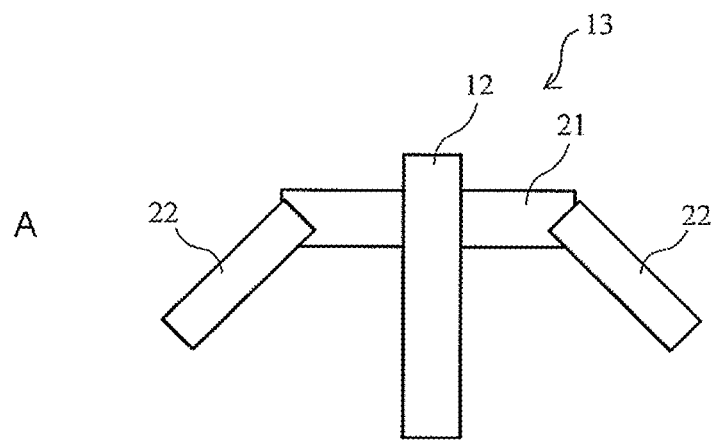
FIG. 2 is a diagram illustrating a schematic configuration example of the rotor 13 according to another embodiment of the centrifuge 10.

FIG. 2 is a diagram illustrating a schematic configuration example of a rotor 13 according to another embodiment of the centrifuge 10. FIG. 2A is a diagram illustrating an appearance of the rotor 13 of the another embodiment.

The rotor 13 in FIG. 2 is an angle-type rotor, and includes a rotation shaft 12, a rotating disk 21 connected to the rotation shaft 12, and a plurality of buckets 22 provided to the rotating disk 21 (see FIG. 2A). Each of the buckets 22 holds sample separation device 100.

<Configuration of Sample Separation Device 100>

Figure 3:
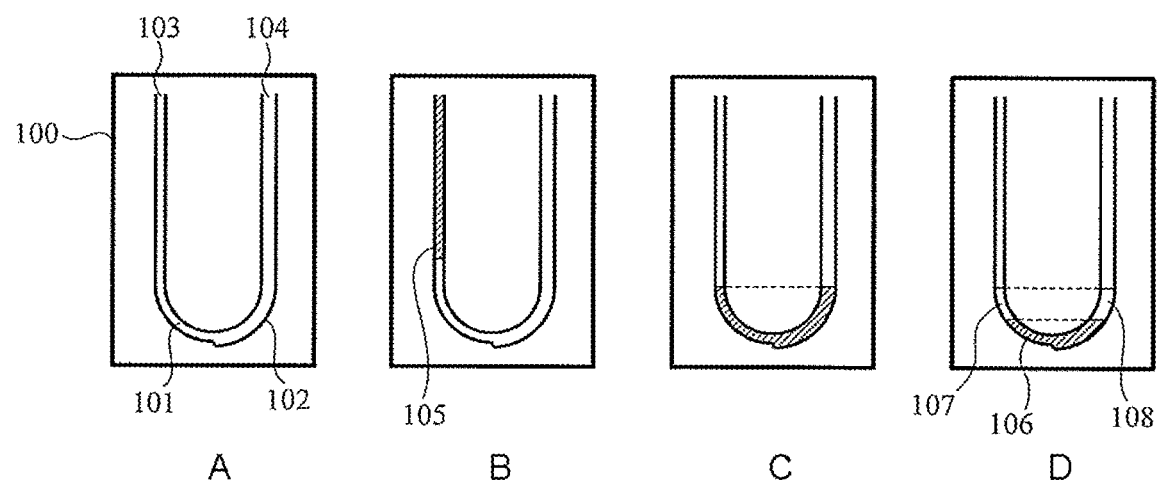
FIGS. 3A to 3D are diagrams illustrating a configuration example of a sample separation device 100 according to the embodiment of the present disclosure.

FIG. 3 is a diagram illustrating a configuration example of the sample separation device 100 according to the embodiment of the present disclosure. FIGS. 3A to 3D illustrate a process before an introduced blood (sample) is separated into each blood cell component.

As illustrated in FIG. 3A, the sample separation device 100 is formed of a U-shaped flow path, and the width of a flow path 102 on the right side is larger (the thickness, diameter, or cross-sectional area is larger) than a flow path 101 on the left side on the drawing sheet. In the sample separation device 100 illustrated in FIG. 3A, the size of the flow path is made different at the substantially central portion of the U-shaped flow path, but it is not necessary that the size is made different at the central portion. The portion at which the size is changed may be further on the left side (side closer to a sample introduction port 103) or further on the right side (side closer to a collection port 104 of the separated liquid component).

<Procedure of Sample (Blood Cell) Separation>

Figure 4:
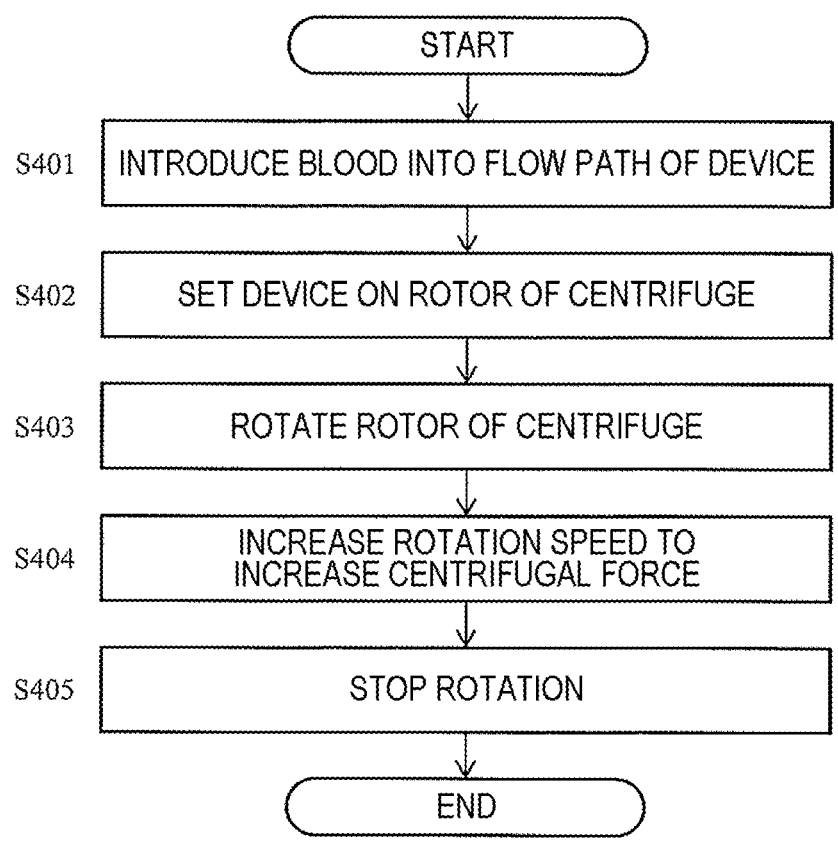
FIG. 4 is a flowchart for describing a procedure of sample separation.

FIG. 4 is a flowchart for describing a procedure of sample separation. With reference to FIGS. 3 and 4, each step of the procedure of blood cell separation will be described.

(i) Step 401

As illustrated in FIG. 3B, a certain amount of blood (sample) 105 is introduced through the sample introduction port 103 on the left side of the flow path. The amount of the blood 105 to be introduced is determined in advance according to, for example, the size of the tube (flow path) of the sample separation device 100.

(ii) Step 402

The sample separation device 100 into which blood has been introduced is set on the rotor 13 illustrated in FIG. 1 or FIG. 2. At this time, the sample separation device (U-shaped flow path) 100 is arranged so that the bottom surface thereof comes to the bottom surface side of the bucket 22.

(iii) Step 403

The rotor 13 of the centrifuge 10 is rotated. When the rotor 13 of the centrifuge 10 is rotated, a centrifugal force is applied to the sample separation device 100 in the direction of the bottom surface of the U-shaped flow path. Then, as illustrated in FIG. 3C, the blood moves to the lower side of the U-shaped flow path, and the blood upper surfaces are located at the same height in the left and right flow paths. Because the width of the right flow path is larger, more blood is present in the right flow path.

(iv) Step 404

The rotation speed of the rotor 13 of the centrifuge 10 is increased to further increase the centrifugal force. Then, as illustrated in FIG. 3D, blood cells 106 and plasmas 107 and 108 are separated, and the interfaces between the blood cells and the plasmas are located at the same height in the left and right flow paths.

(v) Step 405

The rotation of the rotor 13 of the centrifuge 10 is stopped. Because the width of the right flow path is larger, more plasma 108 is present in the right flow path. After the rotation is stopped, the plasma 108 present in the right flow path is collected and used for analysis.

EXAMPLES

Hereinafter, examples of the sample separation device 100 described above will be described.

(1) Example 1

Figure 5:
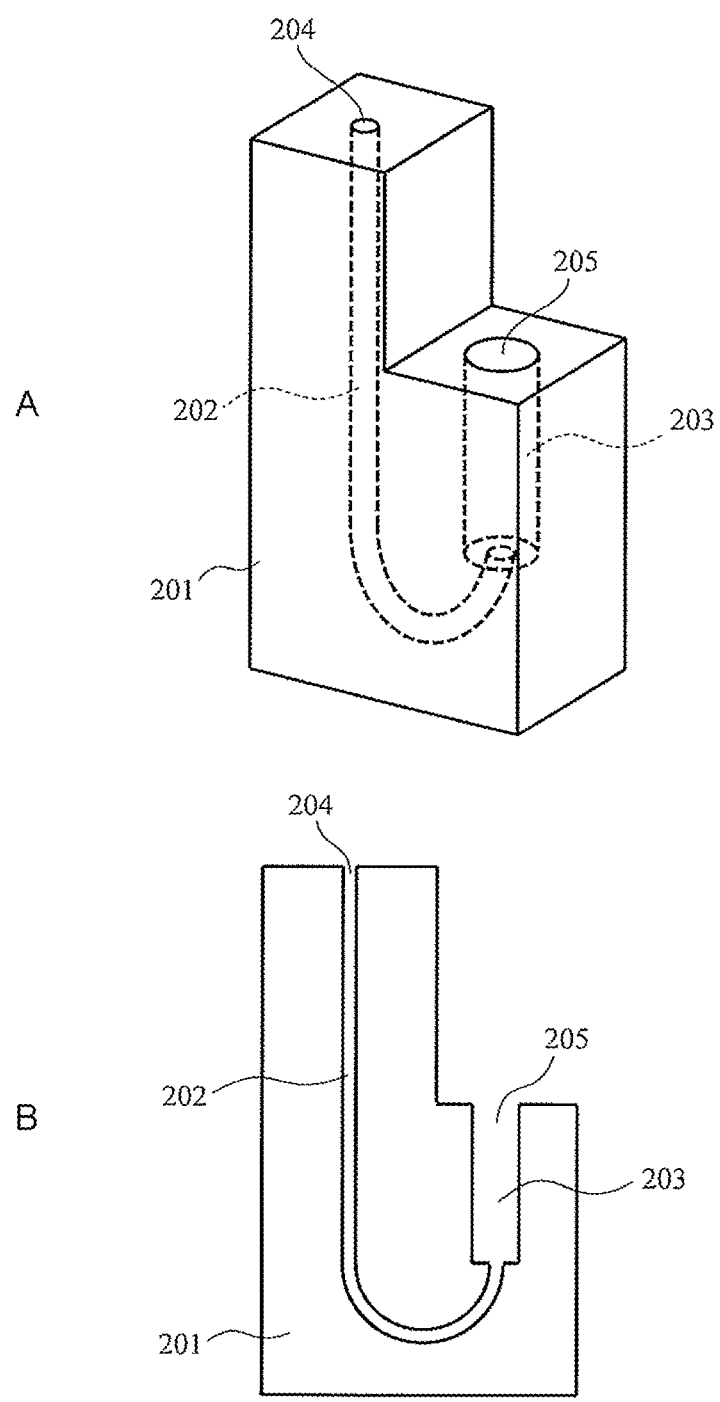
FIGS. 5A and 5B are diagrams illustrating a configuration example of a blood cell separation device 201 using an asymmetric U-shaped flow path (J-shaped flow path) according to Example 1.

FIG. 5 is a diagram illustrating a configuration example of a blood cell separation device 201 using an asymmetric U-shaped flow path (J-shaped flow path) according to Example 1. FIG. 5A is a diagram illustrating an appearance configuration example of the blood cell separation device 201. FIG. 5B is a diagram illustrating a cross section of the blood cell separation device 201.

As illustrated in FIG. 5A, a flow path is formed in the blood cell separation device 201, and a straight tube portion 203 thicker than a J-shaped thin tube portion 202 is connected to the thin tube portion 202. The reason why the J-shape is adopted is that the ease of collection of plasma after blood cell separation is taken into consideration. For convenience, one end of the thin tube portion 202 is referred to as a blood introduction port 204 and one end of the straight tube portion is referred to as a plasma collection port 205 here.

FIG. 6 is a diagram illustrating a procedure of blood cell separation using the blood cell separation device 201. Each step of blood cell separation will be described with reference to FIGS. 4 and 6.

(i) Step 401

First, blood 301 is introduced through the blood introduction port 204. FIG. 6A illustrates a case where the blood is introduced until the thin tube portion 202 is filled by a capillary force. However, the amount of the blood 301 to be introduced varies as appropriate. In addition, a certain amount of the blood 301 may be introduced using a syringe or the like.

(ii) Step 402

The blood cell separation device 201 into which the blood 301 has been introduced is set on the rotor 13 of the centrifuge 10. When the rotor 13 of the centrifuge 10 illustrated in FIG. 1 is employed, the blood cell separation device 201 is set in a horizontal state. On the other hand, when the swing-type rotor 13 illustrated in FIG. 2 is employed, the blood cell separation device 201 is set on the bucket 22 with the downward direction in the drawing sheet of FIG. 6 facing downward (in a direction perpendicular to the rotating disk 21 of the rotor 13).

(iii) Step 403

The rotor 13 of the centrifuge 10 is rotated. For example, it is preferred that a centrifugal force be applied by rotation equivalent to 500 g. The centrifugal force is applied to the blood cell separation device 201 in the downward direction in the drawing sheet of FIG. 6 (in a direction horizontal to the rotating disk 21 of the rotor 13).

Then, the blood moves in the flow path due to the centrifugal force, and the blood is introduced into the straight tube portion 203 as illustrated in FIG. 6B. At this time, as shown by the broken lines, the upper surfaces of the blood of the thin tube portion 202 and the straight tube portion 203 substantially coincide with each other.

(iv) Step 404

In the state of step 403 (see FIG. 6B), the rotation speed of the rotor 13 is increased to increase the centrifugal force (for example, equivalent to 1,100 g). Then the blood begins to separate.

(v) Step 405

The rotation of the rotor 13 of the centrifuge 10 is stopped. Then, as illustrated in FIG. 6C, the blood is clearly separated into blood cells 302 and plasmas 303 and 304.

Referring to FIG. 6C, the blood cells 302 and the plasmas 303 and 304 are separated in both the thin tube portion 202 and the straight tube portion 203. Since the cross-sectional area of the straight tube portion 203 is larger than the cross-sectional area of the thin tube portion 202, more blood is present in the straight tube portion 203 on the right side in the state of FIG. 6B. Therefore, even in the state of FIG.

6C after the separation, more plasma 304 exists on the straight tube portion 203 on the right side.

FIG. 6D illustrates a state in which the separated plasma 304 is dispensed by a probe 305. The probe 305 is connected to a liquid transfer mechanism (not shown) such as a syringe pump, for example. For example, the probe 305 is inserted into the straight tube portion 203 using a robot (not shown), and the plasma 304 is aspirated by the syringe pump (not shown). Then, the probe 305 is inserted into a separately prepared measurement cell, and the aspirated plasma is discharged. At this time, it is necessary to correctly recognize the liquid surface of the plasma 304 and the separation surface between the plasma 304 and the blood cells 302.

Figure 7:
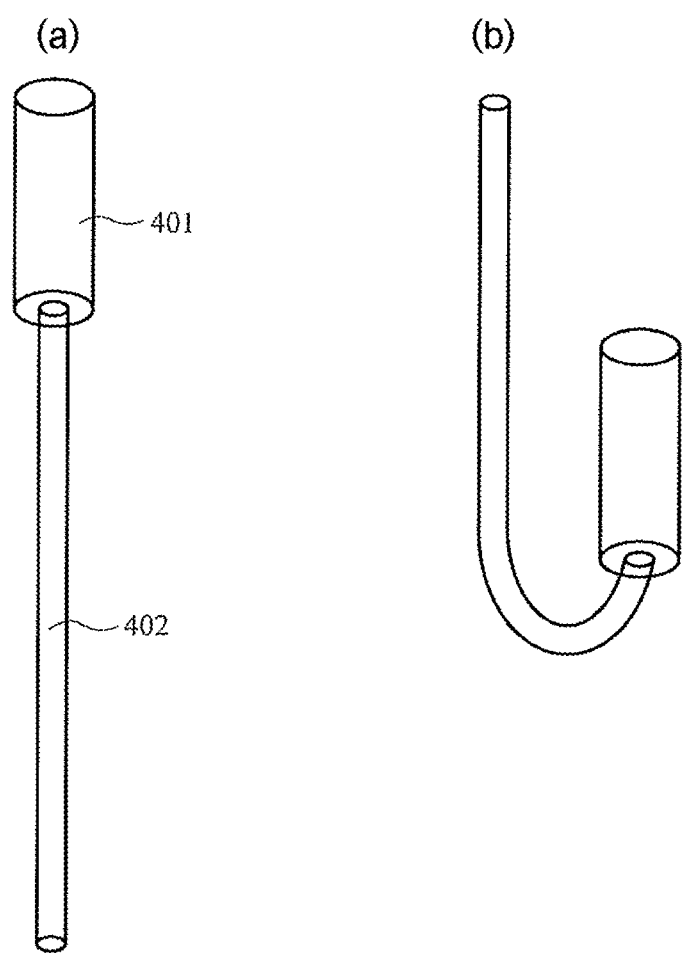
FIGS. 7(a) to 7(b) are diagrams illustrating an example of a method of manufacturing the blood cell separation device 201.

FIG. 7 is a diagram illustrating an example of a method of manufacturing the blood cell separation device 201. First, a member including a straight tube portion 401 and a thin tube portion 402 having a straight shape is prepared (see FIG. 7A). The straight tube portion 401 and the thin tube portion 402 can be made of a plastic tube such as polycarbonate. Next, the thin tube portion 402 is bent to have a J-shape (see FIG. 7B). By placing the member on the rotor 13 in the state of FIG. 7B, a device having substantially the same effect as the blood cell separation device 201 of FIG. 5 is obtained.

In FIG. 7, the straight tube portion 401 and the thin tube portion 402 may be joined by melting one of the tubes by heat, or may be joined by using an adhesive made of the same material as the tubes. Although two tubes having different diameters are joined here, the blood cell separation device may be formed by changing the shape of one tube. For example, the thin tube portion 402 may be formed by heating the end of the tube constituting the straight tube portion 401 and extending the tube, or the straight tube portion 401 may be formed by expanding the end of the tube constituting the thin tube portion 402. However, in this case, although there is no joining portion between the straight tube portion 401 and the thin tube portion 402, an inclination is formed at a portion where the straight tube portion 401 transitions to the thin tube portion 402.

Figure 8:
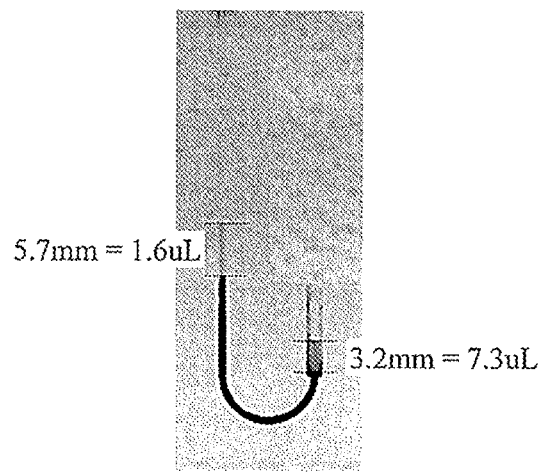
FIG. 8 is a diagram illustrating the results of trial production of the device of FIG. 5 and plasma separation according to the procedure of FIG. 6.

FIG. 8 is a diagram illustrating the results of trial production of the device of FIG. 5 and plasma separation according to the procedure of FIG. 6. When 20 μL of blood was introduced through the introduction port, and 1,100 g was applied for 10 minutes by the centrifuge, the blood cells and the plasma were separated as illustrated in FIG. 8. Initially, it was assumed that the liquid surfaces of the plasma would coincide with each other on the left and right sides of the flow path. However, the result was that the liquid surface on the narrow side of the J-shaped flow path was high. This was assumed to be due to a capillary force. In the case of hydrophilicity, the thinner the diameter, the larger the capillary force acts, so that the liquid level on the thin side rises until the difference in gravity is balanced between the left and right sides of the flow path.

Figure 9:
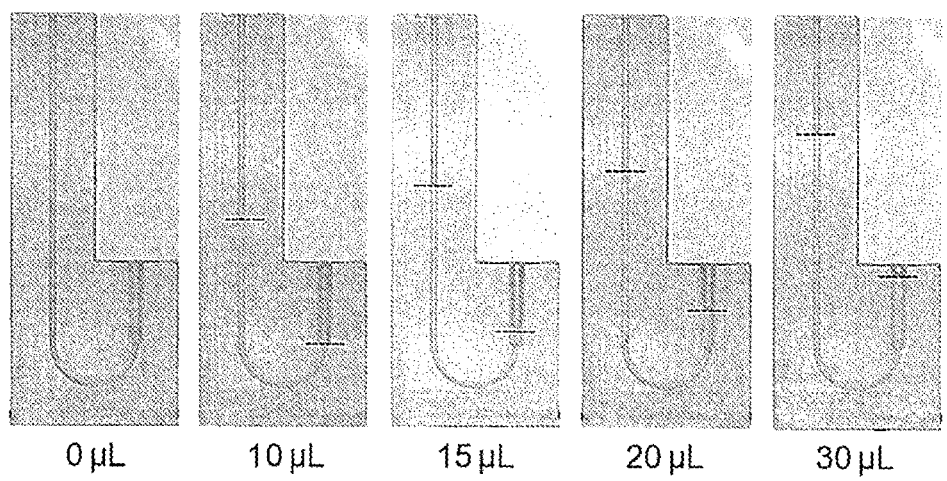
FIG. 9 is a diagram illustrating the result of adding 10 to 30 μL of pure water to the plasma separation device and examining the relationship between the liquid amount and the liquid surface level.

For verification, the relationship between the liquid amount and the liquid surface level was examined using an aqueous solution sample. 10 to 30 μL of pure water was added to the plasma separation device and observed (FIG. 9). In each case, the liquid surface on the small diameter side was located higher than the liquid surface on the large diameter side, and the difference was 16.8±1.1 mm. The rise of the liquid due to the capillary force in the capillary is given by the following equation. A raised height h of the liquid is expressed as Equation 1 when a contact angle θ (the angle between the rising of the liquid surface due to surface tension and the horizontal plane), a surface tension T, a tube diameter r, a liquid density ρ, and a gravitational acceleration g are defined.

[Equation 1]

$$h = \frac{2T \cos \theta}{\rho g r} \qquad \text{Equation 1}$$

The difference between the raised heights on the small diameter side and the large diameter side is a raised height on the small diameter side. Using a contact angle of 66 degrees on a flat plate of the same material as the plasma separation device, the calculated value was 16.0 mm. From the coincidence with the experimental results within the error range, it was concluded that the liquid was raised by the capillary force.

When the centrifugal force of 1100 g is applied, the liquid does not rise very much. This is because, in the equation, when the gravitational acceleration increases, the rising height decreases. In other words, this indicates that the observed liquid rising occurs after the completion of centrifugation. Since the movement of the liquid after centrifugation disturbs the plasma separation interface and lowers the resolution, it is necessary to suppress the rise of the liquid in order to maintain the resolution. In addition, if the amount of rising of the liquid changes due to a change in the interfacial tension between the flow path and the blood, the liquid surface level on the large diameter side also changes. Thus, it is necessary to consider the liquid surface level when collecting the plasma, which complicates the collecting operation.

In order to suppress the rising of the liquid due to the capillary force, the diameter of the tube may be increased at the portion where the rising is required to be suppressed. This is hereinafter referred to as a diameter change portion (liquid surface defining portion). This structure resembles a capillary stop valve often used in rotary cartridges, but operates differently. In the capillary stop valve, the liquid flowing from the small diameter side stops due to the interfacial tension at the portion where the diameter changes. If the liquid overcomes the interfacial tension by applying a centrifugal force or the like and once flows, the interfacial tension is lost and the function as a valve is lost. On the other hand, the device according to the present disclosure utilizes the balance between the gravity and the capillary force, and does not utilize the interfacial tension at the diameter change portion. In other words, after the blood is introduced into the device and centrifuged, the device is set to be vertical and the gravity acts on the liquid in the downward direction of the device, whereas the capillary force of the device thin tube acts on the liquid and causes the liquid to rise. Since the gravity and the capillary force are balanced, the function of preventing the rising of the liquid is maintained even if the liquid flows once to wet the flow path surface in the diameter change portion and lose the interfacial tension. Therefore, there is an advantage that the liquid may be introduced from the side where the diameter of the diameter change portion is large. In fact, in the designed device, the blood is introduced from the side where the diameter is large.

Figure 19:
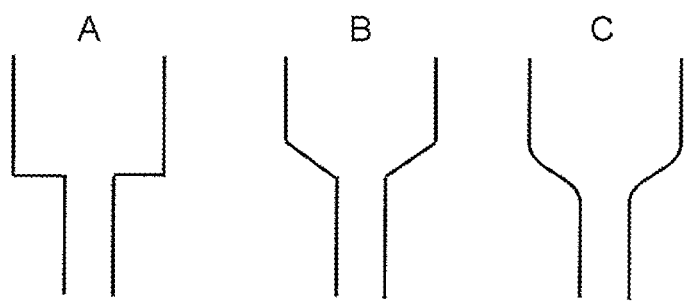
FIGS. 19A to 19C are diagrams illustrating the feature of the method of controlling a position of a liquid surface by increasing the diameter to reduce a capillary force and balance the capillary force with the gravity, unlike a capillary stop valve that uses the interfacial tension at the portion where the diameter changes.

In the above example, as illustrated in FIG. 19A, the diameter change portion was formed with a bend of about 90 degrees (the diameter is not changed gradually but changed abruptly). However, as illustrated in FIGS. 19B and 19C, the diameter may be bent at an obtuse angle or bent continuously (changed gradually). As described above, FIG. 19 illustrates the feature of the method of controlling the position of the liquid surface by increasing the diameter to reduce the capillary force and balance the capillary force with the gravity, unlike the capillary stop valve that uses the interfacial tension at the portion where the diameter changes.

A plasma separation device in which the thickness of the small-diameter-side flow path was discontinuously increased to 1.7 mm was produced, and plasma separation was performed under the same conditions (FIG. 10). Although the liquid surface on the small diameter side was located higher than the liquid surface on the large diameter side, the rising of the liquid surface on the small diameter side stopped at a point where the tube became thick. The separated plasma amount was 2.1 µL on the small diameter side and 7.7 µL on the large diameter side. The amount of plasma increased on both the left and right sides as compared with the case without the diameter change portion. This is because disturbance of the plasma separation interface is reduced by suppressing the rising of the liquid at the diameter change portion. The device illustrated in FIG. 10 was designed to process 20 µL of blood (example).

Plasma separation was performed using plasma separation devices having a diameter change portion designed for a blood amount of 10 µL (FIG. 11). The rising of the plasma was suppressed by the diameter change portion. In the four devices having the same shape, the obtained plasma amount was 1.2±0.1 µL on the small diameter side and 3.9±0.4 µL on the large diameter side. The height of the interface between the plasma and the blood cells did not coincide between the small diameter side and the large diameter side, and the height was higher on the large diameter side. The devices in FIG. 11 were designed to process 10 µL of blood (example).

Assuming that sedimentation of the blood cells due to the centrifugal force occurs independently on the left and right sides of the asymmetric U-shaped flow path, a phenomenon in which the interface height does not coincide between the small diameter side and the large diameter side can be described. The reduction will be described with reference to FIG. 12. When the centrifugal force is applied vertically downward while 10 µL of blood is introduced into the flow path, the liquid surface of the blood is aligned horizontally on the left and right, so that 2.1 µL of blood is present on the small diameter side and 7.9 µL of blood is present on the large diameter side with the lowermost portion of the flow path set as the reference (the reference position is set to 0). When the application of the centrifugal force is continued, the blood cells sediment and the plasma is separated. In the blood used in this experiment, the ratio of the blood cells to the plasma was 1:1. Therefore, the interfaces between the blood cells and the plasma appear at a position of 1.05 µL to the left side of the reference position and a position of 3.85 µL to the right side of the reference position. On the left side of the reference position, the interface is located at the middle point because the thickness of the tube is constant, whereas on the right side of the reference position, the interface is located on the large diameter side with respect to the middle because the small diameter portion and the large diameter portion are present. Therefore, the interface is located higher on the large diameter side than on the small diameter side. After the centrifugation, the liquid moves to the small diameter ide due to the rising due to the capillary force, but the amount of movement is only 2.3 µL-2.1 µL=0.2 µL, which is the volume between the liquid surface on the small diameter side and the capillary stop valve during the centrifugation. In conclusion, it is calculated that the separation interface on the smaller diameter side is located at a position of 1.05 µL from the capillary stop. It almost coincides with the plasma amount on the small diameter side of 1.2±0.1 µL, which is the experimental result.

The above discussion yielded two important findings for cartridge design. One is that by providing the diameter change portion on the small diameter portion side of the J-shaped flow path, it is possible to suppress the rising of the liquid due to the capillary force. The other is a plasma separation model in which, when whole blood is centrifuged, separation occurs independently on the left and right sides of the J-shaped flow path.

Figure 13:
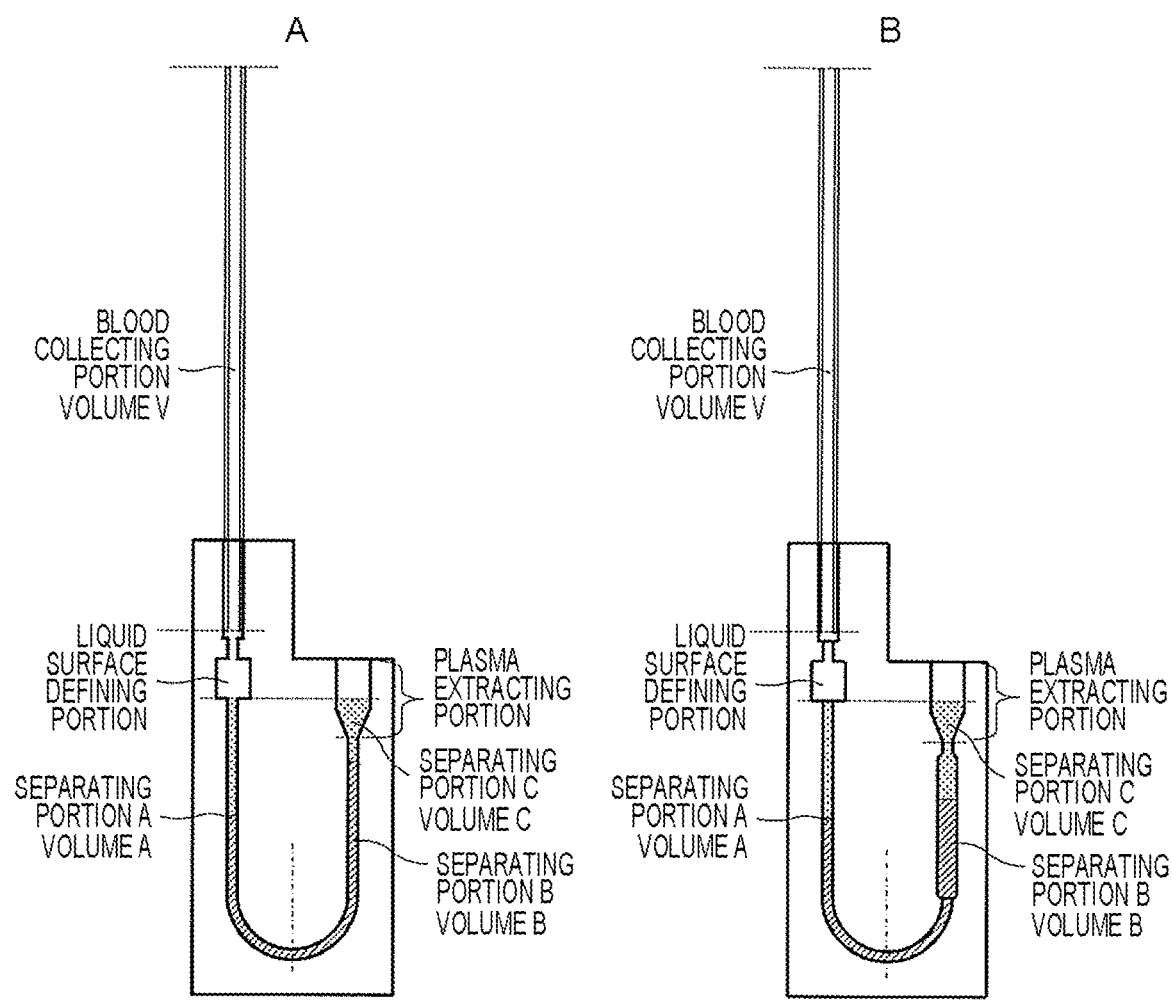
FIGS. 13A to 13B are diagrams illustrating an example of a plasma separation device.

The present disclosure provides a technology that enables plasma to be easily extracted from a single drop of blood. In the case of plasma separation as illustrated in FIG. 11, when the blood plasma is collected with a needle-shaped probe, it is necessary to accurately grasp the position of the interface and drive the probe with a precise operation. If this operation is simplified and it is only required to insert the probe to perform aspiration without considering the position of the interface, the structure of the probe-related device can be simplified. FIG. 13 is a diagram illustrating examples of a device that makes this possible. Utilizing the fact that the plasma extracting port includes a large diameter portion and a small diameter portion, the interface always comes to the small diameter portion. In this case, it is possible to always collect only the plasma simply by arranging the probe slightly above the portion where the diameter changes and aspirating the specified amount.

One point of the device configuration is to prevent the liquid rising due to the diameter change portion. If the volume of the flow path below the height of the diameter change portion is taken as the volume of the collected blood, the liquid surface at the plasma extracting port is always at the height of the diameter change portion. Therefore, the amount of liquid present in the large diameter portion of the plasma extracting port is always constant, and it is not necessary to measure the liquid surface at the time of collecting with the probe.

FIG. 13 is a diagram illustrating examples of a plasma separation device. FIG. 13A is for 10 µL of blood and FIG. 13B is for 20 µL of blood. As illustrated in FIG. 13, there are defined a blood collecting portion (also called a liquid collecting portion), a liquid surface defining portion (diameter change portion), a separating portion A, a separating portion B, a separating portion C, and a plasma extracting portion. Since the liquid surface defining portion has a smaller horizontal cross-sectional area (assuming that gravity is applied from below to above in the drawing sheet) than the separating portion A, the rising of the liquid stops near the connecting portion between the liquid surface defining portion and the separating portion A. When the volumes of the separating portions A, B, and C are A, B, and C, respectively, and the volume of the blood collecting portion is V, if the design is made so that A+B+C=V, a liquid surface on a plasma extracting portion side is located on the same horizontal plane as the liquid surface defining portion. Even if the relationship of A+B+C=V slightly deviates due to manufacturing errors, the liquid surface on the left side of the drawing sheet is defined near the connecting portion between the liquid surface defining portion and the separating portion A, so that the liquid surface at the plasma extracting portion also becomes almost constant. As a result, there is no need to detect the plasma liquid surface when collecting the plasma with the probe.

Another point of the device configuration is that based on the plasma separation model in the J-shaped flow path, only the plasma is separated at the plasma extracting portion. The separation interface between the plasma and the blood cells varies with the percentage of blood cells. This percentage of the blood cells is called the hematocrit value, and the maximum value in normal values is 51.8%. Since the actual separation interface has a gap between blood cells, it is increased by about 10% to 30% of this value (when it is increased by about 10%: $\alpha=0.57$, when it is increased by about 20%: $\alpha=0.62$, and when it is increased by about 30%: $\alpha=0.67$). That is, the blood cell volume after the separation is about 70% at the maximum. In order for the separation interface to always come to the small-diameter portion on the plasma extracting port side, the small-diameter portion may be 70% of the volume on the plasma extracting port side.

When the volume of the blood cells after centrifugation in the whole blood is $\alpha$, if B and C are set so that the relationship of $(B+C)\times\alpha\leq B$ is satisfied, the separation surface between the blood cells and the plasma is located in the separating portion B, and only the plasma is present at the plasma extracting portion. According to the plasma separation model, since plasma separation occurs independently in the separating portion A, the separating portion B, and the separating portion C, the blood cell volume after centrifugation in the separating portion B side and the separating portion C side is $(B+C)\times\alpha$. If this value is equal to or smaller than B, the blood cells fall into the separating portion B, and only the supernatant plasma is present in the separating portion C. As a result, it is not necessary to detect the interface between the plasma and the blood cells when collecting the plasma with the probe. That is, with the device of FIG. 13, it is possible to aspirate only the plasma by inserting the probe into the plasma extracting portion and aspirating the same amount as or a smaller amount than the volume C, thereby being capable of simplifying the plasma collection operation by the probe.

Figure 14:
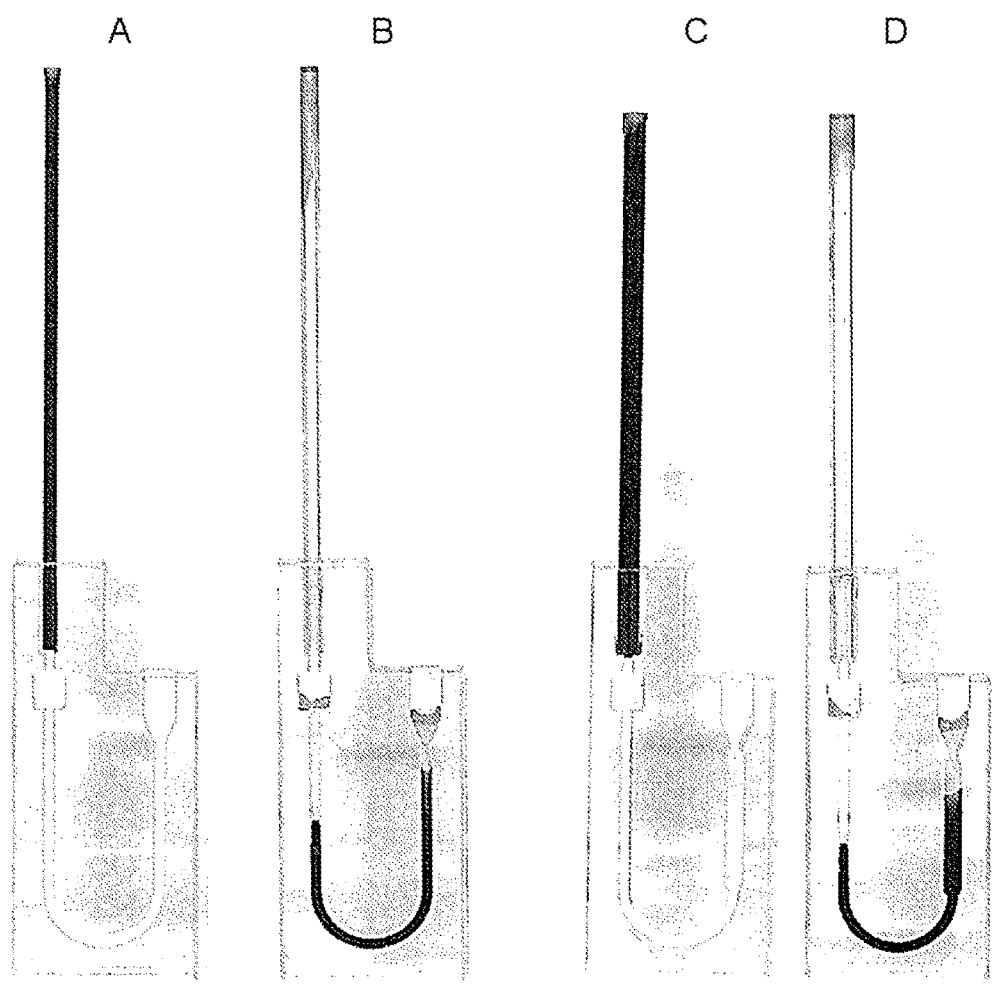
FIGS. 14A to 14D are diagrams illustrating the results of prototyping plasma separation devices, and collecting and centrifuging 10 μL or 20 μL of blood.

A plasma separation device was prototyped, and 10 μL or 20 μL of blood was collected and centrifuged. FIGS. 14A and 14C illustrate a state in which 10 μL or 20 μL of blood is collected, and FIGS. 14B and 14D illustrate a state in which separation is performed by applying a centrifugal force. As illustrated in FIGS. 14B and 14D, the separation interface falls into the separating portion B. When a specified amount of plasma was collected from the plasma extracting portion with the probe, only the plasma was collected.

(2) Example 2

Figure 15:
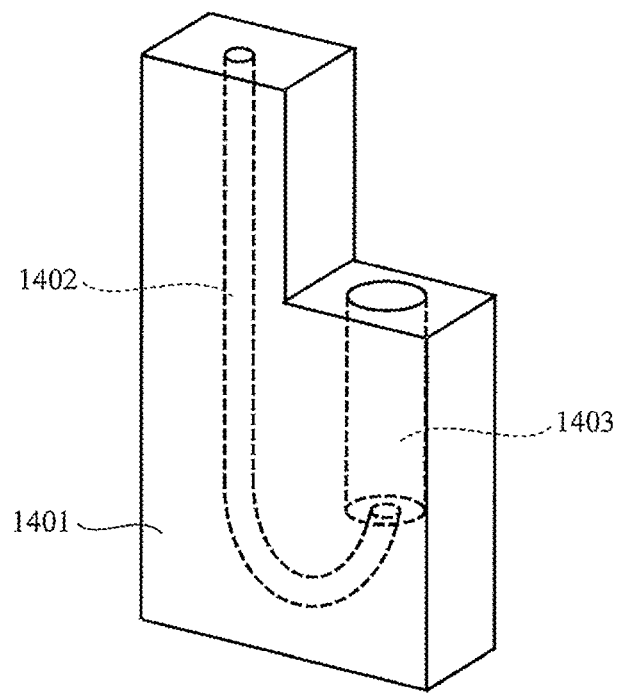
FIG. 15 is a diagram illustrating a configuration example of a blood cell separation device 1401 according to Example 2.

FIG. 15 is a diagram illustrating a configuration example of a blood cell separation device 1401 according to Example 2. Similarly to Example 1 (FIG. 5), the blood cell separation device 1401 includes a J-shaped thin tube portion 1402 and a straight tube portion 1403 that is connected to the thin tube portion 1402 and is thicker (larger in cross-sectional area) than the thin tube portion 1402. However, the difference from Example 1 is that the horizontal cross section of the straight tube portion 1403 has an elliptical shape.

Figure 18:
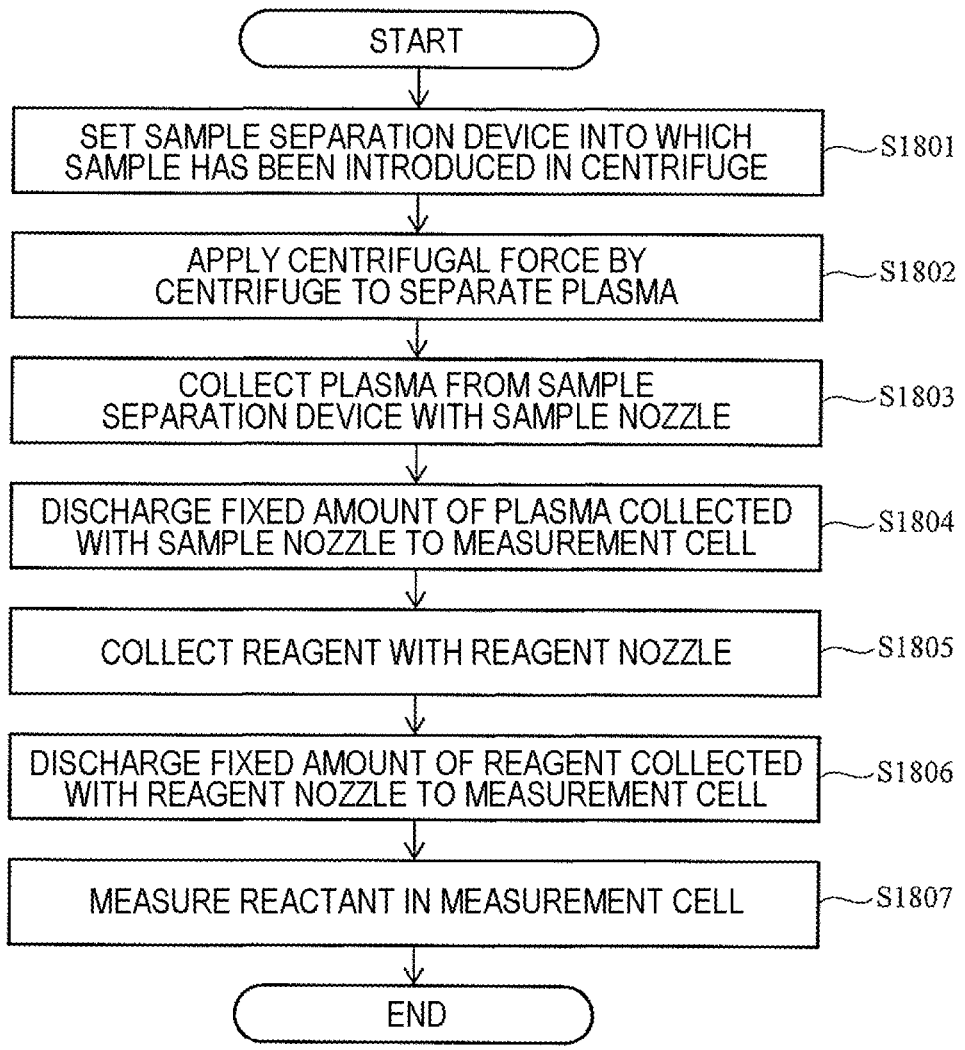
FIG. 18 is a diagram illustrating an example of a measurement flow using the blood analyzer illustrated in FIG. 17.

Here, an example is given in which the horizontal cross section of the straight tube portion 1403 is elliptical, but the straight tube portion 1403 may employ various shapes as long as the cross-sectional area is larger than thin tube portion 1402. For example, as illustrated in FIG. 18, the thickness of the flow path may be constant at the thin tube portion 1502 and the straight tube portion 1503 as viewed in the direction of the arrow X, or the U-shaped portion of the thin tube portion 1502 may be bent at a right angle.

(3) Example 3

Figure 16:
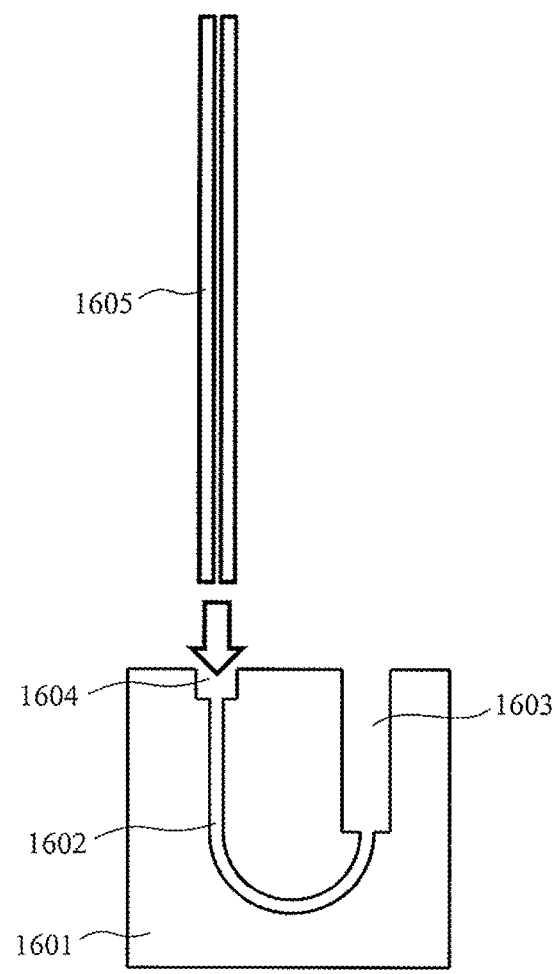
FIG. 16 is a diagram illustrating a configuration example of a blood cell separation device 1601 according to Example 3.

FIG. 16 is a diagram illustrating a configuration example of a blood cell separation device 1601 according to Example 3. Similarly to Example 1 (FIG. 2), the blood cell separation device 1601 includes a J-shaped thin tube portion 1602, a straight tube portion 1603 that is connected to the thin tube portion 1602 and is thicker (larger in cross-sectional area) than the thin tube portion 1602, and a recess 1604 for connecting a capillary blood collection tube 1605 to the blood cell separation device 1601. The capillary blood collection tube 1605 can be detachably attached (set) to the recess 1604. That is, in a state where the capillary blood collection tube 1605 is set, substantially the same configuration and function as the blood cell separation device 201 according to Example 1 (FIG. 2) can be exhibited.

Figure 17:
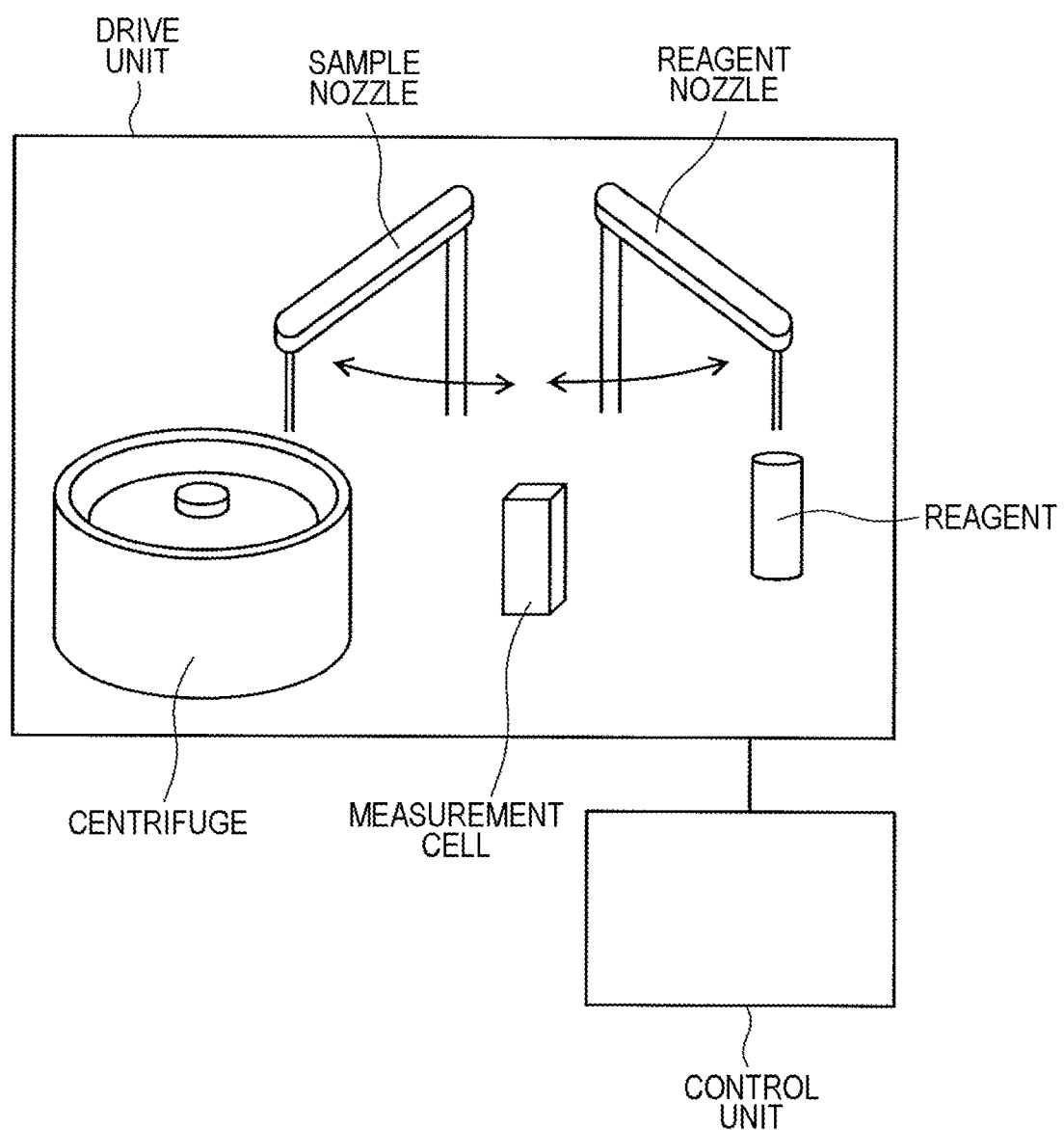
FIG. 17 is a diagram illustrating a configuration example of a blood analyzer.

FIG. 17 is a diagram illustrating a configuration example of a blood analyzer. The blood analyzer includes, for example, a drive unit and a control unit. The drive unit includes a centrifuge, a sample nozzle, a measurement cell, a reagent nozzle, and a reagent storage unit.

FIG. 18 is a diagram illustrating an example of a measurement flow using the blood analyzer illustrated in FIG. 17. A sample separation device into which a sample has been introduced is set in the centrifuge (step 1801). The centrifuge applies a centrifugal force to the sample separation device to separate the plasma into a plasma extracting portion (step 1802). Plasma is collected from the plasma extracting portion of the sample separation device using the sample nozzle (step 1803). Here, when the interface between the blood cells and the plasma is located below the plasma extracting portion as illustrated in FIG. 13, only the plasma can be collected from the plasma extracting portion without considering the position of the interface between the blood cells and the plasma. Then, a fixed amount of the collected plasma is discharged to the measurement cell (step 1804). A reagent is collected using a reagent nozzle (step 1805), and is discharged to the measurement cell in a fixed amount (step 1806). A reaction occurs by mixing the reagent and the sample (plasma), the resulting reaction is measured optically or electrically or any other means (the configuration used for measurement is not illustrated), and the concentration of the substance corresponding to the reagent is quantified (step 1807). A sample separation device arrangement unit may be provided instead of the centrifuge. In this case, a device subjected to centrifugation by a device other than the present device is arranged in the sample separation device arrangement unit.

SUMMARY (i) If the sample (for example, blood) is separated into each liquid component (blood cell, plasma, and serum) using the sample separation device according to the present disclosure, the upper surface of the sample becomes a surface perpendicular to the direction in which the centrifugal force acts. Therefore, more liquid components are collected on the side of the flow path having a large cross-sectional area. As a result, more than half of the desired liquid components (for example, plasma) can be stored on the side of the flow path having a large cross-sectional area. By using the desired liquid component (plasma) obtained on the side having the larger cross-sectional area for analysis, more desired liquid components (plasma) can be used for analysis than in the conventional method. As a result, the amount of the required sample (blood) can be reduced, and therefore, the burden on a person who provides the sample (for example, a patient whose blood is collected) can be reduced.

(ii) An embodiment of the present disclosure discloses a sample separation device used to introduce a sample to be separated to an inside of the sample separation device, centrifuge the sample, and collect a desired liquid after separation, the sample separation device including:

- a sample introducing portion (blood collecting portion) configured to introduce the sample to be separated into the sample separation device;
- a liquid surface defining portion (diameter change portion) connected to the sample introducing portion;
- a first separating portion (separating portion A) connected to the liquid surface defining portion;
- a second separating portion (separating portion B) connected to the first separating portion;
- a third separating portion (separating portion C) connected to the second separating portion; and
- a liquid extracting portion (plasma extracting portion) including the third separating portion and connected to the third separating portion,
- in which a tubular flow path is formed by at least the first separating portion and the second separating portion,
- in which an opening of the sample introducing portion and an opening of the liquid extracting portion are oriented in the same direction,
- in which the first separating portion is configured so that gravity and a capillary force generated in a direction opposite to the gravity act on the sample after separation,
- in which a horizontal cross-sectional area of the liquid surface defining portion is larger than a horizontal cross-sectional area of the first separating portion, and an action of the capillary force on the sample after the separation is reduced when the sample after the separation reaches a lowermost portion of the liquid surface defining portion due to the capillary force. By using the sample separation device having such a configuration, it is possible to avoid a situation in which the sample rises after the sample is separated and the amount of the separated sample (for example, plasma) that can be extracted is less than a desired amount. Since the opening of the sample introducing portion and the opening of the liquid extracting portion are oriented in the same direction, as the premise, the sample separation device is set in the centrifuge in a substantially vertical state (in FIG. 13, the blood collecting portion is above and the separating portions A and B are below). In other words, the sample separation device is not used in a horizontal state (in FIG. 13, the blood collecting portion, the liquid surface defining portion, the separating portions A to C, and the plasma extracting portion are placed at the same height), but the device is used so that the gravity acts on the sample contained in the separating portions (flow path) of the device.

Further, in the sample separation device according to the present embodiment, a horizontal cross-sectional area of a connecting portion between the second separating portion and the third separating portion is the smallest in the third separating portion. Further, a maximum value of the horizontal cross-sectional area of the liquid surface defining portion is equal to or larger than a minimum value of a horizontal cross-sectional area of the third separating portion (see FIG. 13). With this configuration, a capillary force can be applied to the connecting portion between the second separating portion and the third separating portion, and it is possible to reduce the amount of the sample after the separation drawn into the second separating portion from the third separating portion due to the influence of the capillary force acting on the first separating portion.

As can be seen from FIG. 13, the third separating portion forms a part of the liquid extracting portion, and occupies, in the liquid extracting portion, from the connecting portion with the second separating portion to a portion at the height of the liquid surface of the sample after the separation. At this time, a height of the lowermost portion of the liquid surface defining portion is located between an uppermost portion and a lowermost portion of the liquid extracting portion. Further, the height of the lowermost portion of the liquid surface defining portion is the same as the height of the liquid surface of the sample after the separation, which is an uppermost portion of the third separating portion. Therefore, the sample separation device is configured such that, when a volume of the sample introducing portion is V, a volume of the first separating portion is A, a volume of the second separating portion is B, and a volume of the third separating portion is C, A+B+C is substantially equal to V. By configuring the sample separation device such that such a relationship (A+B+C=V) is satisfied, the rising of the sample after the separation can be stopped near the connecting portion between the lowermost portion of the liquid surface defining portion and the first separating portion.

In the sample separation device, it is preferable that a U-shaped or J-shaped flow path is formed by at least the first separating portion and the second separating portion.

The sample to be processed is, for example, blood, and the separated sample extracted from the liquid extracting portion at this time is plasma. When a blood cell volume ratio is $\alpha$, a relationship of $(B+C) \times \alpha \leq B$ is satisfied. Here, a is 0.518, 0.57, 0.62, or 0.67. With this, the separation surface between blood cells and plasma can be located in the third separating portion, and only plasma can be extracted from the plasma extracting portion.

The third separating portion may be configured such that a horizontal cross-sectional area is gradually reduced toward a connecting portion between the third separating portion and the second separating portion. Further, the liquid surface defining portion may be configured such that a horizontal cross-sectional area is gradually reduced from at least a part of the liquid surface defining portion to the lowermost portion.

(iii) The present embodiment also discloses a sample separation method of introducing a sample to be separated to an inside of a sample separation device, centrifuging the sample, and collecting a desired liquid after separation. The sample separation method includes:

preparing the sample separation device and introducing a reagent into a sample introducing portion, the sample separation device including: the sample introducing portion configured to introduce the sample to be separated into the sample separation device; a liquid surface defining portion connected to the sample introducing portion; a first separating portion connected to the liquid surface defining portion; a second separating portion connected to the first separating portion; a third separating portion connected to the second separating portion; and a liquid extracting portion including the third separating portion and connected to the third separating portion, in which a horizontal cross-sectional area of the liquid surface defining portion is larger than a horizontal cross-sectional area of the first separating portion, in which a tubular flow path is formed by at least the first separating portion and the second separating portion, and in which an opening of the sample introducing portion and an opening of the liquid extracting portion are oriented in the same direction;

installing the sample separation device into which the sample is introduced on a centrifuge such that an opening of the sample introducing portion and an opening of the liquid extracting portion are oriented in a direction opposite to a gravity acting direction;

operating the centrifuge and applying a centrifugal force to the sample separation device;

stopping the application of the centrifugal force by the centrifuge;

applying gravity and a capillary force generated in a direction opposite to the gravity on the sample after separation in the first separating portion in a state where a posture of the sample separation device is in a direction parallel to a rotation shaft of the centrifuge;

reducing the action of the capillary force on the sample after the separation at a lowermost portion of the liquid surface defining portion; and extracting the sample after the separation from the liquid extracting portion.

REFERENCE SIGNS LIST

100 sample separation device
101 flow path on left side
102 flow path on right side
103 sample introduction port
104 collection port for liquid component after separation

The invention claimed is:

1. A sample separation device used to introduce a sample to be separated to an inside of the sample separation device, centrifuge the sample, and collect a desired liquid after separation, the sample separation device comprising:
   a sample introducing portion configured to introduce the sample to be separated into the sample separation device;
   a liquid surface defining portion connected to the sample introducing portion;
   a first separating portion disposed below the liquid surface defining portion and connected to the liquid surface defining portion;
   a second separating portion connected to the first separating portion;
   a third separating portion disposed above the second separating portion and connected to the second separating portion; and
   a liquid extracting portion including the third separating portion and connected to the second separating portion,
   wherein a tubular flow path is formed by at least the first separating portion and the second separating portion,
   wherein an opening of the sample introducing portion and an opening of the liquid extracting portion are oriented in a same direction,
   wherein the first separating portion is configured so that gravity and a capillary force generated in a direction opposite to a gravity act on the sample after separation,
   wherein the liquid surface defining portion has a horizontal cross-sectional area which is larger than a horizontal cross-sectional area of the first separating portion,
   such that an action of the capillary force on the sample after the separation is reduced when the sample after the separation reaches a lowermost portion of the liquid surface defining portion due to the capillary force,
   wherein the third separating portion has a horizontal cross-sectional area which is larger than a horizontal cross-sectional area of the second separating portion,
   wherein a horizontal cross-sectional area of a connecting portion between the second separating portion and the third separating portion is the smallest in the third separating portion, and
   wherein a maximum value of the horizontal cross-sectional area of the liquid surface defining portion is equal to or larger than a minimum value of the horizontal cross-sectional area of the third separating portion.

2. The sample separation device according to claim 1, wherein the third separating portion constitutes a part of the liquid extracting portion, and occupies a part of the liquid extracting portion from a connecting portion with the second separating portion to a height of a liquid surface of the sample after the separation,
   wherein a height of the lowermost portion of the liquid surface defining portion is located between an uppermost portion and a lowermost portion of the liquid extracting portion,
   wherein the height of the lowermost portion of the liquid surface defining portion is the same as the height of the liquid surface of the sample after the separation, which is an uppermost portion of the third separating portion, and
   wherein, when a volume of the sample introducing portion is V, a volume of the first separating portion is A, a volume of the second separating portion is B, and a volume of the third separating portion is C, A+B+C is substantially equal to V.

3. The sample separation device according to claim 1, wherein a U-shaped or J-shaped flow path is formed by at least the first separating portion and the second separating portion.

4. The sample separation device according to claim 2, wherein the sample is blood, and
   wherein the sample after the separation extracted from the liquid extracting portion is plasma.

5. The sample separation device according to claim 4, wherein when a blood cell volume ratio is a, a relationship of $(B+C) \times \alpha \leq B$ is satisfied.

6. The sample separation device according to claim 5, wherein $\alpha$ is 0.518, 0.57, 0.62, or 0.67.

7. The sample separation device according to claim 1, wherein the third separating portion is configured such that a horizontal cross-sectional area is gradually reduced toward a connecting portion between the third separating portion and the second separating portion.

8. The sample separation device according to claim 1, wherein the liquid surface defining portion is configured such that a horizontal cross-sectional area is gradually reduced from at least a part of the liquid surface defining portion to the lowermost portion.

* * * * *